United States Patent [19]

Khalil

[11] Patent Number: 6,090,367
[45] Date of Patent: Jul. 18, 2000

[54] POST-TRANSLATIONAL ACTIVATION OF TGF-$\beta_1$ INVOLVING THE TSP-1 RECEPTOR CD36

[75] Inventor: Nasreen Khalil, Winnipeg, Canada

[73] Assignees: Manitoba Cancer Treatment and Research Foundation; The University of Manitoba, both of Winnipeg, Canada

[21] Appl. No.: 08/971,538

[22] Filed: Nov. 17, 1997

[30] Foreign Application Priority Data

May 17, 1995 [GB] United Kingdom ................... 9509957
May 17, 1996 [CA] Canada ..................... PCT/CA96/00311

[51] Int. Cl.$^7$ ................................. A61K 9/12
[52] U.S. Cl. ................ 424/45; 514/2; 530/300; 530/326
[58] Field of Search .................. 424/45; 514/2; 530/300, 326

[56] References Cited

U.S. PATENT DOCUMENTS 4,816,449  3/1989  Hahn ........................................ 514/17
5,770,563  6/1998  Roberts et al. .............................. 514/8

FOREIGN PATENT DOCUMENTS

93/22340  11/1993  WIPO .

OTHER PUBLICATIONS

Khalil et al, post–translational activation of TGF–B1 by rat alveolar macrophages requires plasmin, thrombospondin and TSp–1 receptor, CD36, American Journal of Respiratory and critical care medicine, 1995 international Conference, abstract, 1995.

Stacey Schultz et al. "Thrombospondin Causes Activation of Latent Transforming Growth Factor–$\beta$ Secreted by Endothelial Cells by a Novel Mechanism", The Journal of Cell Biology, vol. 122, No. 4, Aug. 1993, p923–932.

N. Khalil, et al, "Post–Translational Activation of TGF–B, etc." American Journal of Respiratory and Critical Care Medicine, vol. 151, No. 4, Apr. 1995.

*Primary Examiner*—Thurman K. Page
*Assistant Examiner*—Lakshmi Channavajjala
*Attorney, Agent, or Firm*—Schnader Harrison Segal & Lewis LLP

[57] ABSTRACT

A protein called transforming growth factor-beta (TGF-$\beta$) is important in causing the inflammation and progressive scar tissue in pulmonary fibrosis. The TGF-$\beta_1$ isoform is important in the pathogenesis of pulmonary fibrosis. It is usually secreted non-covalently bound to a latency associated peptide (LAP) which renders it biologically inactive. The inactive form is called latent TGF-$\beta_1$ (L-TGF-$\beta_1$). Activation of L-TGF-$\beta_1$ involves L-TGF-$\beta_1$/TSP-1 complex which interacts with the TSP-1 receptor, CD36, to process L-TGF-$\beta_1$ to the mature form in the presence of plasmin. Synthetic or natural CD36 peptides or fragments thereof can be used to prevent activation of TGF-$\beta_1$, in mammalian alveolar macrophages, thereby controlling the inflammation process.

9 Claims, 14 Drawing Sheets

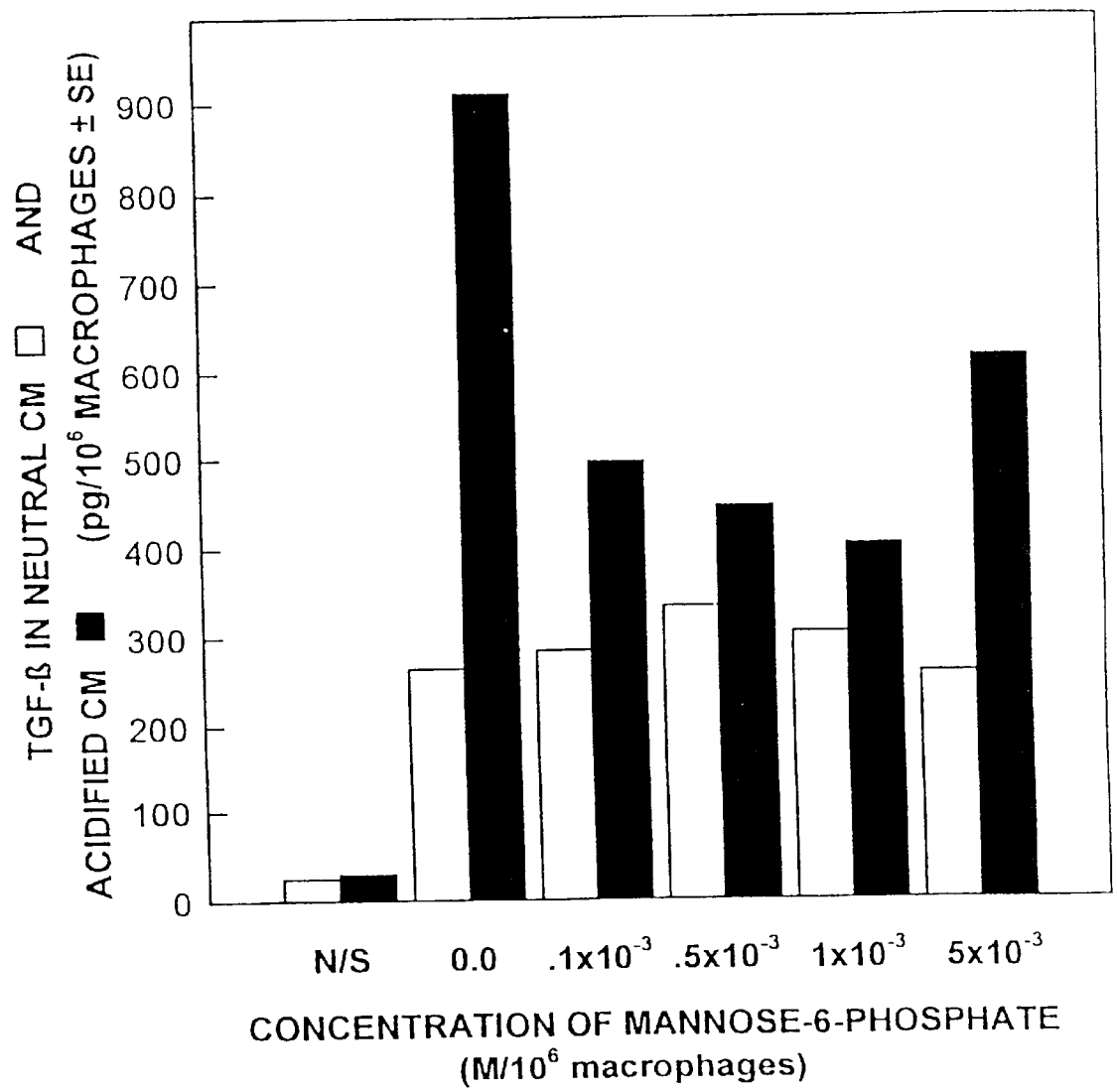
FIG. IA

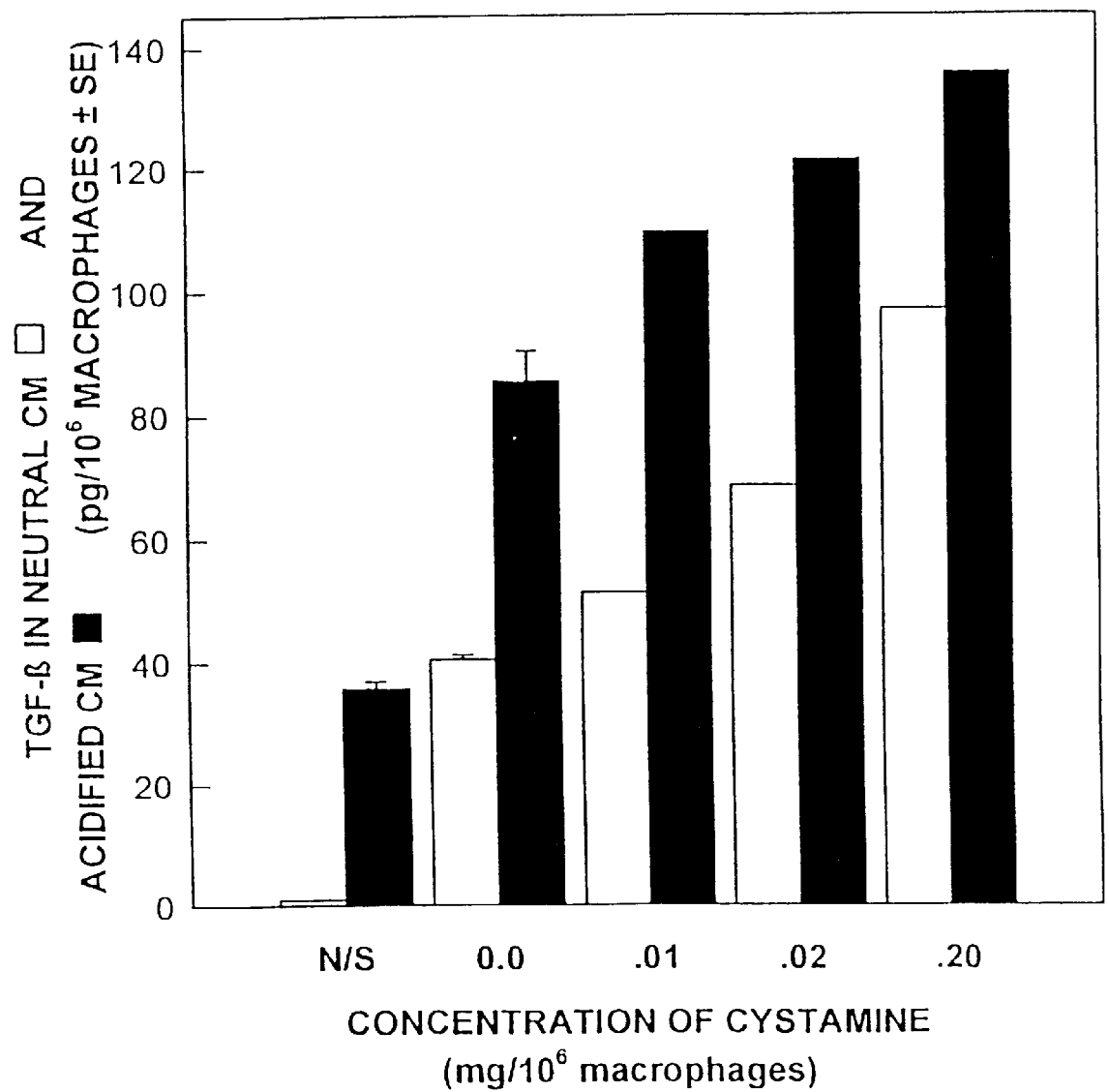
FIG. IB

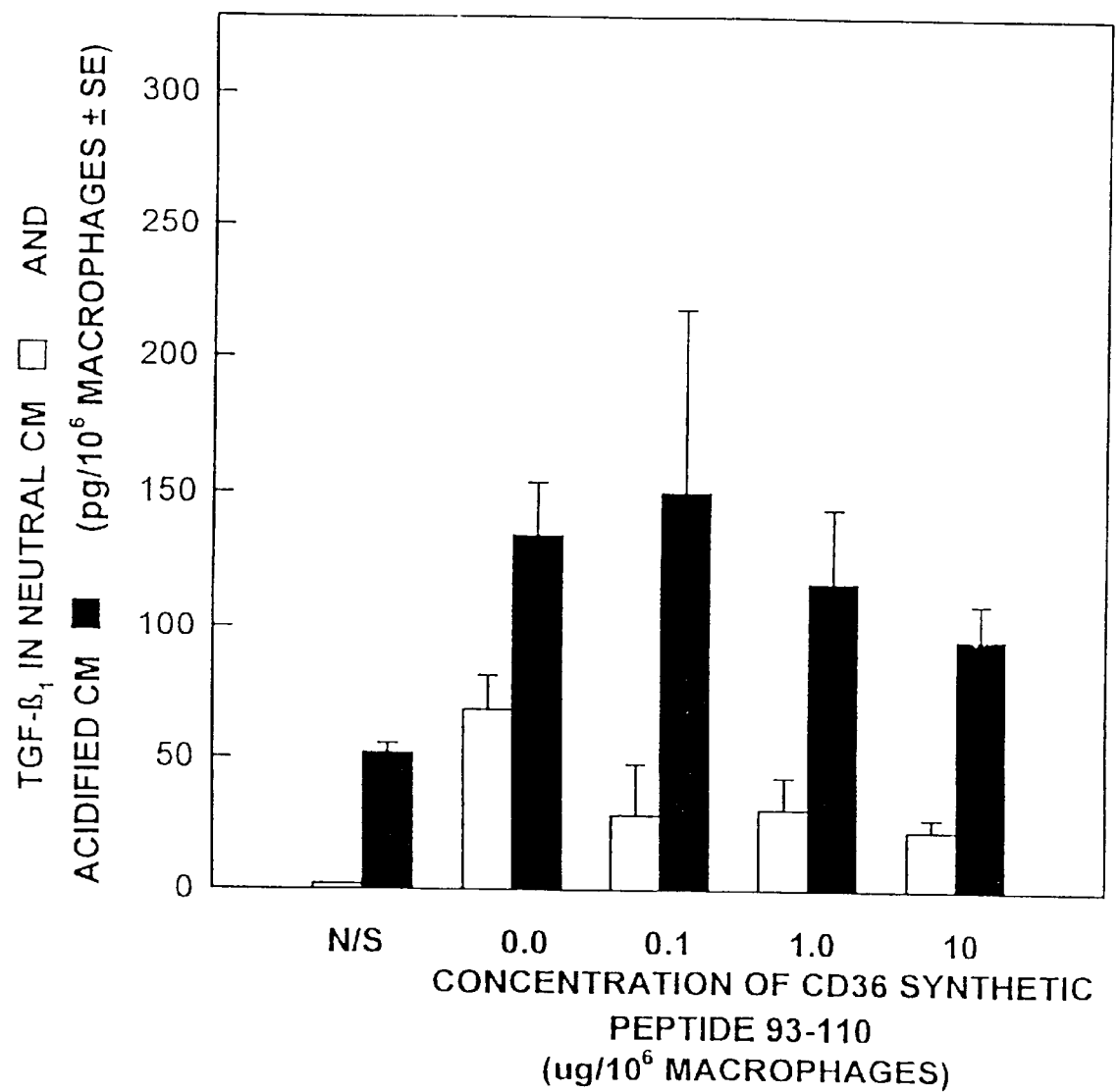
F I G. 6A

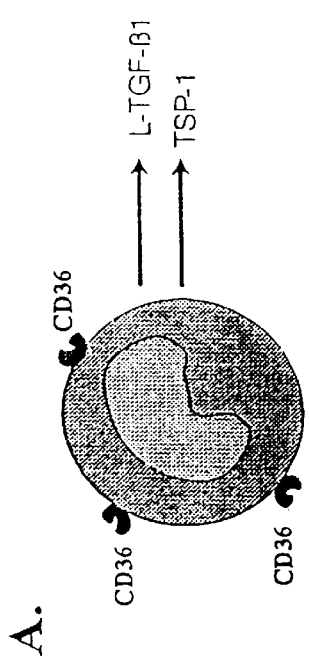
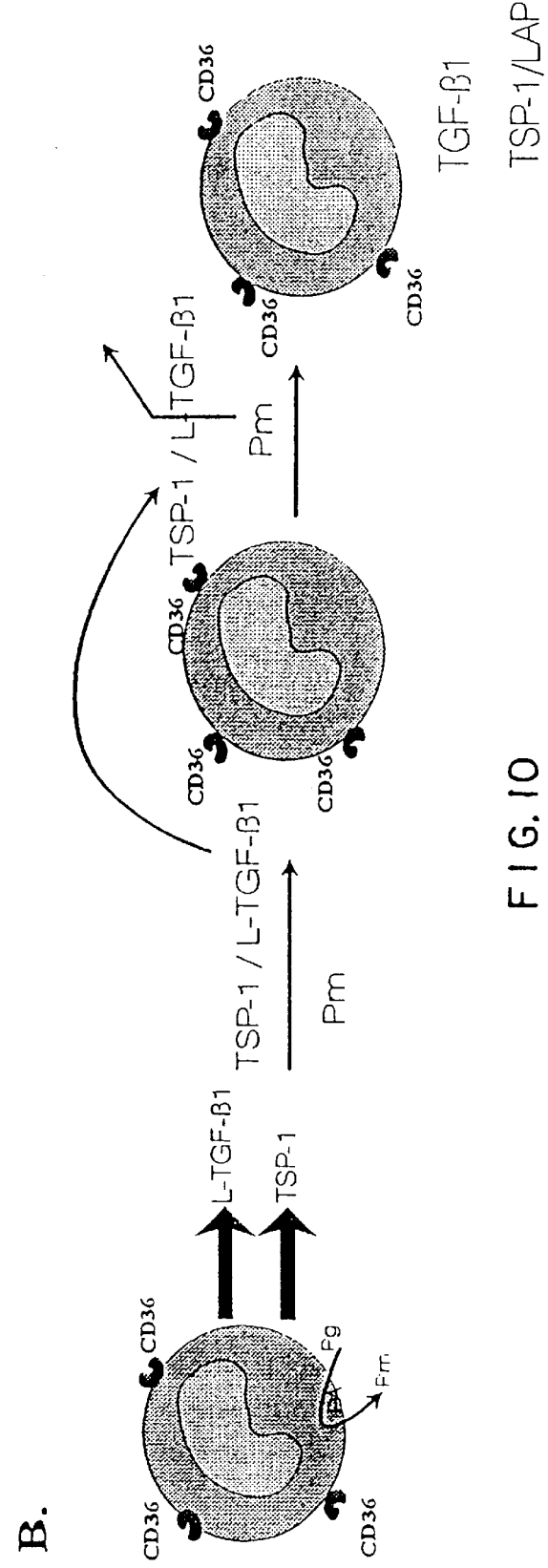
FIG. 10

POST-TRANSLATIONAL ACTIVATION OF TGF-β₁ INVOLVING THE TSP-1 RECEPTOR CD36

BACKGROUND OF THE INVENTION

The present invention relates to a treatment of pulmonary fibrosis which can be caused by a variety of agents and may be associated with a number of diseases. The most common form of pulmonary fibrosis is idiopathic pulmonary fibrosis (IPF). IPF is a progressive and lethal pulmonary disease occurring in between about 9 to 23 people per 100,000 and for which no cure is presently available. Although most physicians generally treat IPF and other fibrotic lung diseases with high doses of corticosteroids, a favourable response rarely occurs, and if it does occur, it is transient. Instead, the use of high dose corticosteroids leads to a variety of complications that can be lethal themselves.

It has been demonstrated that a protein called transforming growth factor-beta (TGF-$\beta$) is important in causing the inflammation and progressive scar tissue in pulmonary fibrosis. The presence of inflammation and scarring lead to morbidity and mortality. TGF-$\beta$ exists in three isoforms in mammals, designated as TGF-$\beta_1$, TGF-$\beta_2$ and TGF-$\beta_3$. The characteristics as well as the in vitro and in vivo biological effects are most extensively reported for TGF-$\beta_1$. Applicants have found that the TGF-$\beta_1$ isoform is important in the pathogenesis of pulmonary fibrosis induced by bleomycin. All cells in the body produce TGF-$\beta$s and all cells can respond to it. However, it is usually secreted non-covalently bound to a latency associated peptide (LAP) which renders it biologically inactive. The inactive form is called latent TGF-$\beta_1$ (L-TGF-$\beta_1$).

Applicants have found that in an animal model of pulmonary fibrosis and in samples from patients with IPF, TGF-$\beta_1$ is secreted by alveolar macrophages in an active form. As well, applicants have found indications that in advanced cases of IPF, active TGF-$\beta_1$ is secreted by epithelial cells. Epithelial cells may be the source of TGF-$\beta_1$ found subepithelially where there is extensive fibrous connective tissue present. The subepithelial location of TGF-$\beta_1$ could result in expansion of the fibroblast cell population and enhanced connective tissue synthesis and therefore play a critical role in the pathogenesis of pulmonary fibrosis.

Others have shown that, even in the presence of corticosteroids, once active TGF-$\beta_1$ is present, it causes fibrosis to occur. Corticosteroids are able to prevent macrophages from entering the lungs, however, applicants have shown that once macrophages are able to secrete active TGF-$\beta_1$, the presence of huge doses of corticosteroids does not inhibit the process. Furthermore, epithelial cells are structural cells and their number is not affected by corticosteroids. Secretion of TGF-$\beta_1$ by epithelial cells is unaffected by corticosteroids, and this fact may explain the relative failure of corticosteroids in treating IPF.

The present invention provides means to prevent macrophages (and other cells) from secreting the active form of TGF-$\beta_1$, thus stopping the inflammation and fibrosis from progressing. Therefore, the present invention may also be useful in the treatment of other diseases that have been associated with abnormal production of TGF-$\beta_1$. These include but are not limited to scleroderma, systemic lupus erythematosis, sarcoidosis, silicosis, asbestosis, tuberculosis, hypersensitivity pneumonitis, keloids, burn induced hypertrophic scarring, cirrhosis of the liver, hypertrophic vetrinopathy, rheumatoid arthritis, Chron's disease, metastatic breast cancer, and other malignancies.

It is of significant clinical importance that:

(1) Although systemic corticosteroids which are standard therapy for the above mentioned diseases decrease the influx of inflammatory cells, they do not alter the secretion of active TGF-$\beta_1$ by macrophages.

(2) In the presence of high systemic corticosteroids, if active TGF-$\beta_1$ is present, it reverses all possible inhibition of enhanced connective tissue synthesis induced by steroids.

(3) The use of high systemic corticosteroids results in severe side effects, morbidity, and possibly even death. The applicants findings suggest that:

I) TGF-$\beta_2$ and TGF-$\beta_3$ proteins (that are the other forms of TGF-$\beta$) are ubiquitously expressed, and ii) TGF-$\beta_3$ may be important in physiological responses to injury, while iii) TGF-$\beta_1$ protein expression is associated with normal and aberrant tissue repair.

These observations would suggest that in disorders mediated by excessive inflammation dominated by or regulated by macrophages (examples of which disorders are given above) and aberrant expression of TGF-$\beta_1$, there would be a favourable outcome if the effects of TGF-$\beta_1$ were inhibited. An approach to doing this may be by preventing latent-TGF-$\beta_1$ (L-TGF-$\beta_1$) from being activated.

Macrophages are mononuclear phagocytes derived from the bone marrow. Although macrophages are recognized for their ability to phagocytose foreign particles and tissue debris, macrophages also have an important role in wound repair. At sites of injury, prior to connective tissue synthesis, there is an influx of activated macrophages. When activated, macrophages secrete a number of pro-inflammatory and fibrogenic cytokines such as platelet derived growth factor (PDGF), interleukin-1 (IL-1), IL-6, tumour necrosis factor-alpha (TNF-$\alpha$), basic fibroblast growth factor (bFGF), as well as TGF-$\beta$. Of these cytokines, TGF-$\beta$ is one of the most potent regulators of inflammation and connective tissue synthesis.

In the context of wound repair, TGF-$\beta_1$ is a potent chemoattractant for macrophages and induces these cells to express PDGF, IL-1, b-FGF, TNF-$\alpha$ and TGF-$\beta_1$ itself. These effects of TGF-$\beta_1$ on macrophages suggest that TGF-$\beta_1$ at a site of injury can result in a macrophage dominated inflammatory infiltrate and subsequently enhanced connective tissue synthesis.

The main cellular source of most connective tissue proteins are fibroblasts. In vitro, TGF-$\beta_1$ induces proliferation of immature fibroblasts and is a potent chemoattractant of mature fibroblasts and thereby in vivo could increase the number of fibroblasts in an area where TGF-$\beta_1$ is present. Furthermore, TGF-$\beta_1$ induces fibroblasts and other cells to synthesize, secrete and stabilize extracellular matrix proteins such as the collagens.

TGF-$\beta_1$ is synthesized as a large 390 amino acid precursor that undergoes a number of intracellular processing steps that include cleavage of the LAP from the mature TGF-$\beta_1$ protein. However, with rare exception when TGF-$\beta_1$ is secreted by cells, it remains non-covalently associated in a 1:1 ratio with its LAP. The non-covalent association of TGF-$\beta_1$ with its LAP renders the TGF-$\beta_1$ biologically inactive. Since TGF-$\beta_1$ and its receptors are ubiquitously expressed and since TGF-$\beta_1$ has numerous biological effects, the ability of a cell to activate L-TGF-$\beta_1$ upon secretion may be an important regulatory mechanism of TGF-$\beta_1$ action in vivo. In vitro, the LAP can be dissociated from the mature peptide by a number of non-physiological conditions such as extremes of pH, boiling, and chaotropic agents. Other substances that may be more physiological, such as plasmin and thrombospondin-1, can also activate L-TGF-$\beta_1$. In addition, a variety of substances, when cultured in the presence of certain cell lines, can induce the cultured cells to secrete active TGF-$\beta$. For example, when high levels are present of D-glucose in cultures of a murine mesangial cell line or glucocorticoids in cultures of an osteoblast-like cell line, there is secretion of active TGF-$\beta$ into the conditioned media (CM). The physiological relevance of this post-translational activation of L-TGF-$\beta$ in these in vitro systems is unclear.

In a well characterized rat model of pulmonary injury and fibrosis,. induced by the antineoplastic antibiotic, bleomycin, it has been demonstrated that total lung TGF-$\beta$ was markedly increased seven days after bleomycin administration, when it was localized almost exclusively to alveolar macrophages. When alveolar macrophages were prevented from entering the lungs with high systemic doses of corticosteroids, this enhanced expression of total lung TGF-$\beta$ was abrogated. It has also been demonstrated that soon after bleomycin administration, explanted alveolar macrophages were induced to generate a biologically active form of TGF-$\beta_1$ and plasmin, the generation of which was maximal seven days after bleomycin administration.

Furthermore, the secretion of active TGF-$\beta_1$ was totally inhibited by the presence of alpha$_2$-antiplasmin, a naturally occurring inhibitor of plasmin. When large quantities of plasmin were added to activated alveolar macrophages, there was further activation of the L-TGF-$\beta_1$. However, when plasmin was added to the L-TGF-$\beta_1$ present in cell-free conditioned media from the same alveolar macrophages, no further activation of L-TGF-$\beta_1$ occurred. Other findings suggest that the generation of plasmin is important in the post-translational activation of alveolar macrophage derived L-TGF-$\beta_1$ during an inflammatory pulmonary injury response and that the activation required the presence of intact macrophages. Alveolar macrophages isolated from human patients with IPF also demonstrated inhibited production of active TGF-$\beta_1$ in the presence of alpha$_2$-antiplasmin.

Applicants have now found that activation of L-TGF-$\beta_1$ involves L-TGF-$\beta_1$/TSP-1 complex which interacts with the TSP-1 receptor, CD36, to process L-TGF-$\beta_1$ to the mature form in the presence of plasmin. It has also been found that synthetic CD36 peptides can be used to prevent activation of TGF-$\beta_1$ in rat and in human alveolar macrophages, thereby controlling the inflammation process. The present invention, in accordance with these findings, relates to activation of L-TGF-$\beta_1$ and regulation thereof.

The present invention will be more readily illustrated with reference to the following description.

BRIEF DESCRIPTION THE DRAWINGS

FIG. 1: Regulation of alveolar macrophage derived L-TGF-$\beta_1$ by mannose-6-phosphate and cystamine.

A) Seven days after bleomycin administration, alveolar macrophages obtained by bronchoalveolar lavage (BAL) were cultured in the absence or presence of several concentrations of mannose-6-phosphate. TGF-$\beta_1$ was quantitated using the CCL-64 bioassay. TGF-$\beta_1$ in neutral CM (□) represents active TGF-$\beta_1$ while that in acidified then neutralized CM (■) represents total TGF-$\beta_1$ of the same sample. The presence of mannose-6-phosphate had no effect on the quantity of active TGF-$\beta_1$ secreted by alveolar macrophages.

B) Alveolar macrophages obtained in the identical manner as above were cultured in the absence or presence of several concentrations of cystamine. The presence of cystamine stimulated the secretion of both active (□) and latent (■) TGF-$\beta_1$ present in the CM.

FIG. 2: Quantity of TSP-1 secreted by explanted alveolar macrophages obtained from rats at varying lengths of time after bleomycin administration. The quantity of TSP-1 secreted by alveolar macrophages after bleomycin injury was determined by using a direct ELISA and anti-TSP-1 monoclonal antibodies. Alveolar macrophages from normal saline treated rats secreted small amounts of TSP-1. Alveolar macrophages obtained after bleomycin administration secreted increased quantities of TSP-1, the secretion of which was maximal 7 days after administration of bleomycin. Each point is the mean of 2–6 animals.

FIG. 3: The effects of anti-TSP-1 antibody on the activation of alveolar macrophage derived L-TGF-$\beta_1$. Alveolar macrophages obtained 7 days after bleomycin administration were cultured in the absence or presence of varying concentrations of anti-TSP-1 antibody. TGF-$\beta_1$ present in neutral CM (□) represents bioactive TGF while that present in acidified then neutralized CM (■) represents the total TGF-$\beta$ in the same sample. The presence of the anti-TSP-1 antibody inhibited activation of L-TGF-$\beta_1$ in a dose dependent manner. Each point is the mean of 6 animals.

FIG. 4: Activation of alveolar macrophage derived L-TGF-$\beta$ with supplementation of TSP-1.

A) Alveolar macrophages were obtained 7 days after bleomycin administration and cultured. After 12 hours, TSP-1 was added to the cultures of alveolar macrophages. The CM was collected 24 hours later and the TGF-$\beta_1$ in neutral (□) and acidified (■) CM of the same sample was determined. The presence of TSP-1 in CM overlying alveolar macrophages increased the TGF-$\beta_1$ activity in neutral (□) CM but had no effect on the total TGF-$\beta_1$ secreted (■).

B) TSP-1 was added to cell free CM obtained from the above alveolar macrophages and the culture was incubated 24 hours prior to TGF-$\beta_1$ quantitation in neutral (□) and acidified (■) CM. The presence of TSP-1 in cell free CM activated the L-TGF-$\beta_1$ present in solution only at the highest concentration.

FIG. 5: The effects of anti-CD36-antibody on the activation of L-TGF-1-$\beta_1$.

Alveolar macrophages obtained 7 days after bleomycin administration were cultured in the absence or presence of varying concentrations of anti-CD36 antibody. The TGF-$\beta_1$ present in neutral CM (□) and acidified then neutralized CM (■) from the same sample was quantitated. Although the presence of CD36 antibody induced the macrophages to secrete increased amounts of TGF-$\beta_1$, most of it remained in the latent form. The presence of CD36 antibody abrogated activation of L-TGF-$\beta_1$ in a dose-dependent manner. Each point is the mean of 4 samples.

FIG. 6: The effects of CD36 synthetic peptides on the activation of L-TGF$\beta_1$.

A) Alveolar macrophages obtained 7 days after bleomycin administration were cultured in the absence or presence of several concentrations of the synthetic peptides CD36[93-110]. TGF-$\beta_1$ in neutral (□) and acidified then neutralized CM (■) was quantitated. The presence of CD36[93-110] inhibited activation of L-TGF-$\beta_1$ in a dose response dependent fashion.

B) CD36[139-155] peptides had no effect on the activation of L-TGF-$\beta_1$.

C) CD36[204-218] also had no effect on the activation of L-TGF-$\beta_1$.

The concentrations of CD36$^{139-155, 244-288}$ are shown that were the same as an effective CD36$^{93-110}$ concentration. All points are the mean of 2–4 animals.

FIG. 7: The effects of TSP-1 synthetic peptide CSVTCG, and its control scramble peptide, SVTGCC, on the activation of L-TGF-$\beta_1$.

A) The addition of the TSP-1 synthetic peptide CSVTCG in several concentrations was used. The presence of CSVTCG inhibited the activation of L-TGF-$\beta_1$ only in its highest concentration.

B) The presence of SVTGCC had no effect on the activation of L-TGF-$\beta_1$ at any dose.

FIG. 8: Detection of the presence of TSP-1 on alveolar macrophages by FACS analysis seven days after normal saline administration.

A) Alveolar macronhages obtained by BAL were incubated with mouse IgG (anti-TSP-1 isotype control) prior to incubation with the FITC labelled secondary antibody.

B) Alveolar macrophages incubated with anti-TSP-1 antibody demonstrate a minimal increase in TSP-1 on the cell.

C) The presence of CD36$^{93-110}$ synthetic peptide had a minimal effect on the expression of TSP-1 on the cell surface.

FIG. 9: Detection of the presence of TSP-1 on alveolar macrophages seven days after bleomycin administration.

A) Alveolar macrophages obtained by BAL were incubated with IgG (anti-TSP-1 isotype control) prior to incubation with the FITC labelled secondary antibody.

B) Alveolar macrophages incubated with anti-TSP-1 antibody demonstrated a twofold increase in TSP-1 on the cell.

C) The presence of CD36$^{93-111}$ synthetic peptide reduced the TSP-1 association on the cell surface by 50%.

FIG. 10: Proposed model for the activation of alveolar macrophage derived L-TGF-$\beta_1$.

A) Resting alveolar macrophages secrete small amounts of L-TGF-$\beta_1$ and TSP-1 but no plasmin. There is little cell surface TSP-1.

B) After bleomycin induced lung injury, the alveolar macrophages are activated to secrete increased quantities of L-TGF-$\beta_1$, TSP-1 and generate increased quantities of plasmin. TSP-1 associates with the alveolar macrophage L-TGF-$\beta_1$ released in the immediate vicinity of the macrophage. The TSP-1/L-TGF-$\beta_1$ complex then associates with the cell surface of the alveolar macrophage by the CD36 receptor. After association of the TSP-1/L-TGF-$\beta_1$ complex, the plasmin generated by the macrophages releases the TGF-$\beta_1$ from the LAP. TGF-$\beta_1$ is then available to react with its receptor and have a biological effect.

Based on the in vitro effects of TGF-$\beta_1$ on inflammatory cells and connective tissue synthesis, the regulation of alveolar macrophage derived L-TGF-$\beta_1$ in a well recognized model of lung injury and fibrosis induced by the antineoplastic antibiotic, bleomycin, was examined. After bleomycin injury, these macrophages are induced to secrete increased quantities of an active form of TGF-$\beta_1$, the secretion of which subsides rapidly after seven days of treatment while the latent form of TGF-$\beta_1$ continues to be secreted in large quantities 28 days after the bleomycin induced injury.

Both plasmin and TSP-1 have been described as activating L-TGF-$\beta_1$ in vitro. Plasmin activates L-TGF-$\beta_1$ by removing the LAP from the L-TGF-$\beta_1$ complex and releasing the mature form. TSP-1, a large multidomain glycoprotein, activates L-TGF-$\beta_1$ by associating with the LAP and causing a conformational alteration such that there is sufficient exposure of TGF-$\beta_1$ to permit TGF-$\beta_1$ to bind to its receptor and have a biological effect. Furthermore, when these activated alveolar macrophages were cultured in the presence of alpha$_2$-antiplasmin, a naturally occurring plasmin inhibitor, or in the presence of TSP-1 antibodies, there are abrogation of the post-translational processing of L-TGF-$\beta_1$. However, neither plasmin nor TSP-1 in themselves was effective in activating alveolar macrophage derived L-TGF-$\beta_1$ in solution. Rather the presence of intact macrophages was necessary for plasmin and TSP-1 to be effective.

The effect of the presence of cells in activating L-TGF-$\beta$ has previously been described. It has been demonstrated that the activation of L-TGF-$\beta$ requires the interaction of endothelial cells with their pericytes and requires the L-TGF-$\beta$ to bind to the cell surface by mannose-6-phosphate-insulin like growth factor-II receptor (M-6-P/IGF-II-R) or transglutaminases. The isoform of TGF-$\beta$ detected in these studies has not been defined. However, the addition of mannose-6-phosphate (which inhibits the M-6-P/IGF-II-R interaction with its ligand) or cystamine (which inhibits the expression of transglutaminases) to alveolar macrophages has no effect on the activation of L-TGF-$\beta_1$. These findings suggested that the mechanism by which L-TGF-$\beta_1$ associates with the cell surface of alveolar macrophages is not by interacting with M-6-P-IGF-II-R or transglutaminases as previously reported but through a unique mechanism that requires the presence of TSP-1 and the TSP-1 cell surface receptor, CD36.

CD36 is an 88 kDa glycoprotein found on the surfaces of monocytes, megakaryocytes, red blood cells, endothelial cells, mammary epithelial cells and some tumour cell lines. Using a monoclonal antibody to CD36, applicants were to completely abrogate the activation of L-TGF-$\beta_1$, but the quantity of total TGF-$\beta_1$ was markedly increased after interacting with alveolar macrophage associated CD36.

The CD36 receptor is a single polypeptide chain with two short cellular domains, two transmembrane domains and the extracellular domain of the CD36 receptor where the TSP-1 binding sites are located. The binding of TSP-1 to the CD36 receptor has been described as a 2 step process by Leung, L. et al (J. Biol. Chem., 1992, 267:18244). The TSP-1 initially interacts with amino acids 139–155 of CD36. This binding induces a conformational change leading to exposure of a second CD36 binding site present between amino acid sequences 93–110. The binding of TSP-1 with amino acids 93–110 on the CD36 receptor is with high affinity and is responsible for the stability of CD36 TSP-1 interaction. Leung also demonstrated that synthetic peptides mimicking the CD36 amino acid sequences between 93–110 and 139–155 prevented the interaction of TSP-1 with CD36.

When synthetic peptides to the CD36 93–110 region were added to the cultures of alveolar macrophages, the post-translation activation of L-TGF-$\beta_1$ was abrogated. Although, earlier observations suggested that the region of CD36 between 139–155 was also important in the interaction of TSP-1 with CD36, the presence of these peptides had no effect on the activation of alveolar macrophage derived L-TGF-$\beta_1$. In addition, a synthetic peptide mimicking a region unrelated to the areas of TSP-1/CD36 interaction had no effect on activation of L-TGF-$\beta_1$.

There is a conformational dependent epitope on TSP-1 that mediates binding of TSP-1 to CD36 as well as other proteins such as laminin, fibronectin, collagen and plasminogen. This TSP-1 epitope consists of the amino acid sequence CSVTCG and mediates interaction of TSP-1 with CD36 and is reported to be an attachment factor for melanoma cells, endothelial cells, and platelets. The synthetic peptide of CSVTCG inhibits the interaction of TSP-1 with CD36 and prevents platelet adherence. The presence of CSVTCG synthetic peptide prevented activation of the alveolar macrophage L-TGF-$\beta_1$. This suggests that when TSP-1 binds to CD36 at amino acids 93–110, it does so at the TSP-1 region delineated by CSVTCG.

These findings for the first time demonstrate that the concomitant increase in expression of TSP-1 and L-TGF-$\beta_1$ in the presence of the CD36 receptor and plasmin, are all required for the activation of L-TGF-$\beta_1$ by alveolar macrophages obtained after a lung injury. Since the activation of alveolar macrophage derived L-TGF-$\beta_1$ is dependent on TSP-1 and plasmin, which diminish early in the bleomycin injury response, this may result in terminating the activation of alveolar macrophage derived L-TGF-$\beta_1$ as well as its inflammatory and fibrotic effects. Furthermore, since the presence of active TGF-$\beta_1$ parallels the inflammatory changes seen in this model, this indicates that the regulation of inflammation that is mediated by active TGF-$\beta_1$ is dependent on the post-translational activation of alveolar macrochage derived L-TGF-$\beta_1$.

The pathogenesis of inflammation involves relentless progression of inflammation and fibrosis and may involve repeated cycles of injury and activation of L-TGF-$\beta$. Regulation of TGF-$\beta$ activation provides a means of controlling the inflammation process. CD36 peptides as described herein can be used to prevent the activation of TGF-$\beta_1$, thereby controlling the pathogenesis of inflammation.

The most critical mechanism for the regulation of TGF-$\beta_1$ function in vivo is the processing of latent TGF-$\beta_1$ to its biologically active form. In an animal model of pulmonary fibrosis, a new synthetic peptide composed of serveral amino acids has been identified to inhibit the cost-translational activation of latent TGF-$\beta_1$. The new TGF-$\beta_1$ blocker could potentially be used as a therapeutic agent to prevent the adverse effects of active TGF-$\beta_1$ in several interstitial lung diseases.

An aerosolized form of the synthetic peptide could be used for the treatment of diseases where active TGF-$\beta_1$ is present. Examples of such diseases are idiopathic pulmonary fibrosis, scleroderma, systemic lupus erythematosis, sarcoidosis, silicosis, asbestosis and hypersensitivity pneumonitis. It also has potential for treatment of keloids, burn induced hypertropic scarring, cirrhosis of the liver, hypertrophic retinopathy, rheumatoid arthritis, Chron's disease, metastatic breast cancer and perhaps other malignancies.

DETAILED DESCRIPTION OF THE INVENTION

Figure 2:
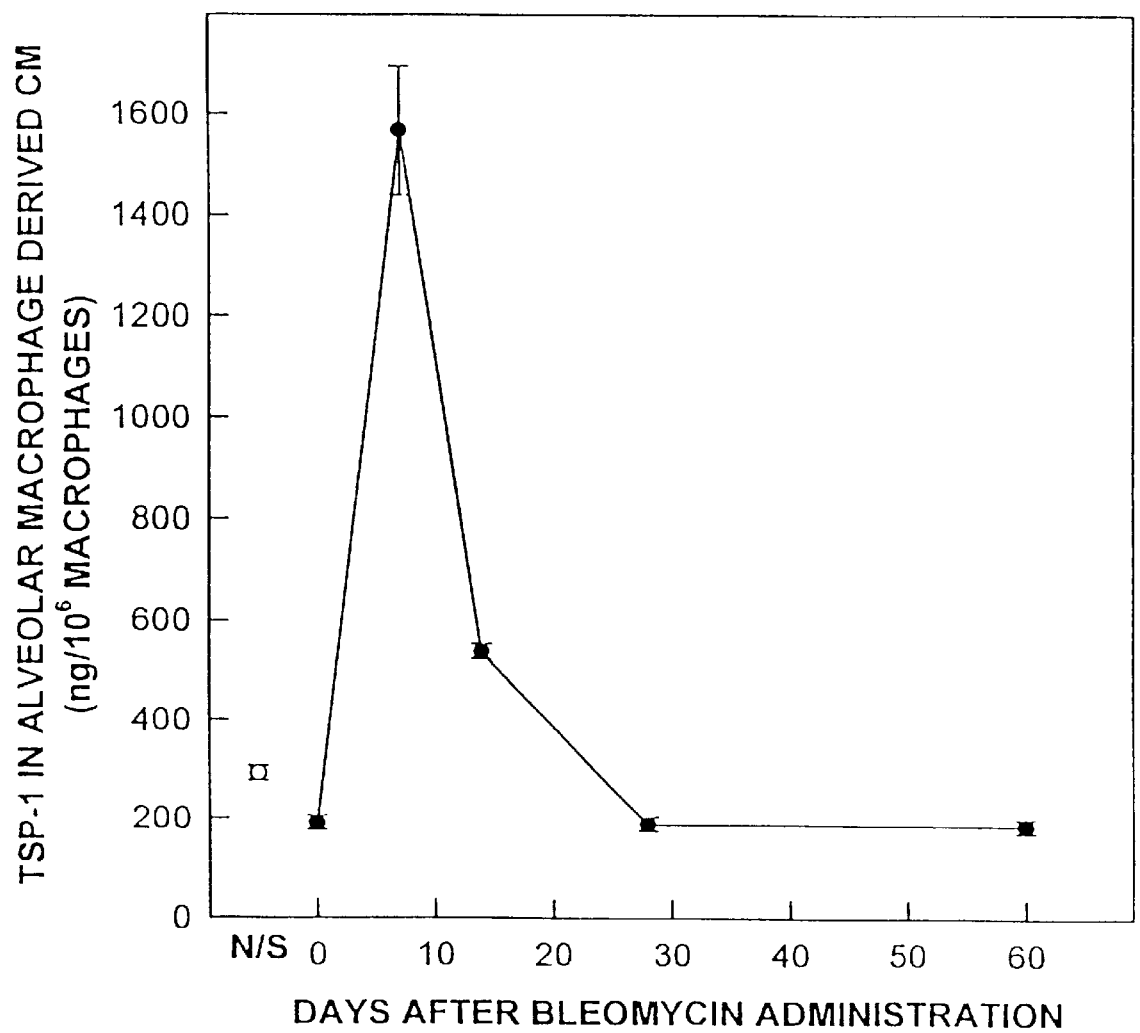

The invention will now be further described and illustrated by means of the following examples.

EXAMPLE 1

Animals: Female Sprague-Dawley rats, which were free of respiratory disease and weighed between 250 and 300 grams, were obtained from the University of Manitoba vivarium. In each experiment, all rats were matched for age and weight.

Reagents: Bleomycin (Blenoxane) was a gift from Bristol Laboratories (Bristol-Meyers Company, Evansville, Ind.). Neutralizing antibody to TGF-$\beta_{1-3}$ was obtained from Genzyme (Cambridge, Mass.). Manose-6-phosphate, cystamine, and anti-TSP-1 antibody were obtained from Sigma (St. Louis, Mo.). The CD36 antibody, 5Fl was provided by the Fifth International Workshop on Leukocyte Differentiation Antigens. Purified TSP-1 used in these experiments was provided by Dr. J. Murphy-Ullrich.

Bleomycin Administration: Rats were anaesthetized by an intraperitoneal injection of 40 mg/kg of Nembutal (Abbott Laboratories, Toronto, Ontario). Tracheostomy was performed and sterile normal saline containing 1 unit of bleomycin sulfate (Blenoxane, Bristol-Myers Company, Evansville, Ind.) in 400 $\mu$l of normal saline was instilled into the lungs using a 25-gauge needle inserted between cartilaginous rings of the trachea. Control animals received 400 $\mu$l of normal saline only. The tracheal site of surgery was sutured and the rats were allowed to recover until the time of sacrifice. At several intervals after bleomycin or normal saline treatment the rats were sacrificed by giving a lethal dose of Nembutal. A thoracotomy was done to expose the heart and lungs. Systemic blood was removed from the lungs by severing the inferior vena cava and flushing the lungs through the right ventricle with phosphated buffered saline (PBS) until the lungs appeared pearly white. The lungs were then lavaged to obtain cells for culture of alveolar macrophages.

Macrophage Cultures: Alveolar macrophages were obtained by cannulating the trachea, instilling and retrieving 5 ml aliquots of sterile normal saline to an accumulative volume of approximately 50 mls. The entire lavage volume was centrifuged and the cell pellet suspended in alpha-minimal essential medium ($\alpha$-MEM; Gibco, Grand Island, N.Y.) with 1 mg percent of bovine serum albumin (BSA; Sigma). The cell count was adjusted to $1\times10^6$/ml and aliquoted as $3\times10^6$ per 6 mm tissue culture plate (Nunclon, Roskile, Denmark). Viability, determined by the appearance of macrophages by polarized microscopy, was greater than 95%. One plate treated in the identical manner was used for Diff Quick staining to determine the percentage of macrophages present at the time of collection of conditioned media. Phenotyping using Diff Quick staining had previously been correlated with esterase staining of macrophages and consistently demonstrated the presence of 98–100% of the adherent cells to be of the macrophage phenotype.

After adherence the macrophages were cultured in the absence or presence of a number of regents consisting of mannose-6-phosphate, cystamine, anti-TSP-1 antibody, 5F1 (anti-CD36 antibody), CD36 synthetic peptides, or TSP synthetic peptides.

Collection of Conditioned Media (CM): After aliquoting $3\times10^6$ cells per well, the macrophages were allowed to adhere for 2 hours. The plates were then washed with $\alpha$-MEM, the non-adherent cells were counted and subtracted from $3\times10^6$ to give the number of cells remaining in culture. From this point, all cells were cultured in serum-free media containing 20 mM Hepes, Gentamicin (4 mg/100 mls; Roussel, Montreal, Quebec), Fugizone (100 $\mu$l/100 mls; Gibco Laboratories) and 0.2% clotted bovine calf plasma (BCP; National Biological Laboratory Limited, Dugald, MB) in the absence or presence of a reagent (described above). After 24 hours of incubation at 37° C., 95% $CO_2$, the media was collected in the presence of protease inhibitors (leupeptin 0.5 $\mu$g/ml; aprotinin 5 $\mu$g/ml; and pepstatin 1 $\mu$g/ml; all three from United States Biochemical Corp., Cleveland, Ohio), aliquoted and frozen at $-80°$ C. until ready for TGF-$\beta$ quantitation. In some instances CM was collected at 48 hours after a culture period for TGF-$\beta$ quantitation.

CCL-64 Mink Lung Epithelial Growth Inhibition Assay for TGF-$\beta$

CCL-64 mink lung epithelial cells were maintained in α-MEM with 10% fetal bovine serum (FBS). Subconfluent cells were used in the TGF-β growth inhibition assay as described by Danielpour et al (J. Cell Physio., 1989, 138:78–86). Cells were trypsinized and washed with α-MEM in 0.2% BCP and resuspended in α-MEM, 0.2% BCP, 10 mM Hepes at pH 7.4, penicillin (25 μ/ml) and streptomycin (25 μg/ml), and cultured as $5 \times 10^5$ cells per 0.5 ml in 24-well costar dishes (Flow Laboratories, Inc., Mississauga, Ont.). Neutral conditioned media or conditioned media that was acidified and subsequently neutralized in the presence or absence of anti-TGF-β antibodies were added 3 hours later. After 22 hours, the cells were pulsed with 0.25 μCi (5 Ci/mg) of S-[$^{125}$I] iodo 2'-deoxyuridine (Amersham Corp., Arlington Heights, Ill.) for 2–3 hours at 37° C. Cells were then fixed with 1 ml of methanol-acetic acid (3:1) (vol./vol.). After 1 hour at room temperature, the wells were washed twice with 2 ml of 80% methanol. The cells were lysed with 1 ml of 1N NaOH for 30 minutes at room temperature and the $^{125}$I-UdR was counted in a gamma counter (LKB instruments, Gaithersburg, Md.). A standard curve of porcine TGF-$\beta_1$ was included in each assay and data were expressed as picograms of TGF-$\beta_1$ per $10^6$ macrophages, as described. For confirmation of TGF-β activity, neutralizing monoclonal antibody to TGF-$\beta_{1-3}$ (Genzyme, Cambridge, Mass.) was added prior to the addition of the conditioned media and resulted in abrogation of all TGF-β activity.

Detection and Quantitation of TSP-1 by Sandwich ELISA. The wells of a 96 well plate (Nunc, Maxisorp Immuno Plate) were coated with 200 ng/well monoclonal antibody to TSP (Mab 127, IgG2a) in a 200 μl volume of PBS overnight at 4° C. The plate was washed 3 times for 3 min each with 300 μl wash buffer (PBS 0.05% Tween029 0.25% BSA). Non-specific binding sites were blocked with 1% BSA in a wash buffer (250 μl/well for 30 mins. at 37° C. and then washed as above. Samples on a standard curve of TSP-1 (0–200 mg/well) were then incubated in the wells in a 200 μl volume for 1 hr. at 37° C. Wells were then incubated with 4.2 μg/ml alkaline phosphatase conjugated Mab 133 (to TSP) in a 200 μl volume for 1 hr at 37° C. Wells were washed as above and bound enzyme-linked antibody was detected following incubation with 300 μg/ml (200 μl volume) Sigma 104 alkaline phosphatase substrate dissolved in 10% diethanolamine, pH 9.6. The plate was incubated in the dark (1 hr, 37), colour development was stopped by adding 50 μl of 2N NaOH, and absorbance at 405 nm was read using a Bio-Tek ELISA reader.

Preparation of synthetic CD36 and TSP-1 peptides. The following CD36 peptides YRVRFLAKENVTQDAEDNC (93–118), CNLAVAAASHIYQNQFVQ (139–155) and CADGVYKVFNGKDNISKV (208–224) and TSP-1 peptide CSVTCG and the scramble peptide TVSGCC were chosen for synthesis based on the works of Leung (J, Biol. Chem., 1992, 267:18244) and Asch (Biochem. Biophy. Res. Commun., 1992, 182:1208) respectively. The peptides were prepared by solid phase synthesis on an Applied Biosystems model 430 peptide synthesizer using t-butoxycarbonyl chemistry. Cleavage of each peptide from the resin was performed with anhydrous HF at −5° C. in the presence of 10% anisole. The peptides were precipitated with ether, dissolved in 0.25M acetic acid and lyophilized. The peptides were purified by high performance liquid chromatography.

Detection of Cell Surface TSP-1 by Flow Cytometry. $5 \times 10^5$ cells were suspended in a 50 μl buffer (phosphate buffered saline +2% newborn calf serum +0.1% sodium azide) and incubated with 5 μl of flourescein isothiocyanate-labelled monoclonal antibodies for 30 minutes at 4° C. The cells were washed twice and suspended in 0.5 ml of assay buffer. The fluorescence was analyzed on a fluorescence-activated cell sorter scan (Becton, Calif.).

Results. All experiments using animal cells, except for those presented in FIG. 2, were done on alveolar macrophages obtained seven days after intratracheal bleomycin administration since this time interval represented the maximal TGF-$\beta_1$ expression and secretion of active TGF-$\beta_1$ in this model. It had been previously demonstrated that plasmin was important for activation of alveolar macrophage derived L-TGF-$\beta_1$ only when cells were also present but was ineffective on alveolar macrophage derived L-TGF-$\beta_1$ in solution. In previous reports using co-cultures of endothelial cells and pericytes, it was demonstrated that cell surface associated manose-6-phosphate insulin-like growth factor-II receptor (M-6-P/IGF-II-R) and transglutaminase were required for activation of bovine endothelial cell derived L-TGF-β. The presence of mannose-6-phosphate which blocks the M-6-P/IGF-II-R or cystamine which inhibits expression of transglutaminases abrogated activation of L-TGF-β in this co-culture system. However when M-6-P and cystamine in cultures of alveolar macrophages were used, there was no effect on the activation of L-TGF-$\beta_1$ (FIGS. 1A, 1B). These findings suggested that although the cell surface was important for activation of L-TGF-$\beta_1$, it was not by interaction with M-6-P/IGF-II-R or transglutaminases.

Plasmin and thrombospondin have been identified as physiological substances that can activate L-TGF-$\beta_1$. Although it has been demonstrated that plasmin was important to the post-translational activation of L-TGF-$\beta_1$, in concomitant experiments, it was desired to determine if TSP-1, a large trimeric glycoprotein, has a role in the post-translational activation of alveolar macrophage derived L-TGF-$\beta_1$.

First, it was determined if alveolar macrophages generated TSP-1 after bleomycin injury. Although alveolar macrophages constitutively secrete TSP-1, the secretion was increased and was maximal seven days after bleomycin administration (FIG. 2). The secretion of TSP-1 declined rapidly thereafter and by 28 days after bleoycin administration the quantity of TSP-1 was equivalent to that secreted by macrophages from normal saline treated rats.

Figure 3:
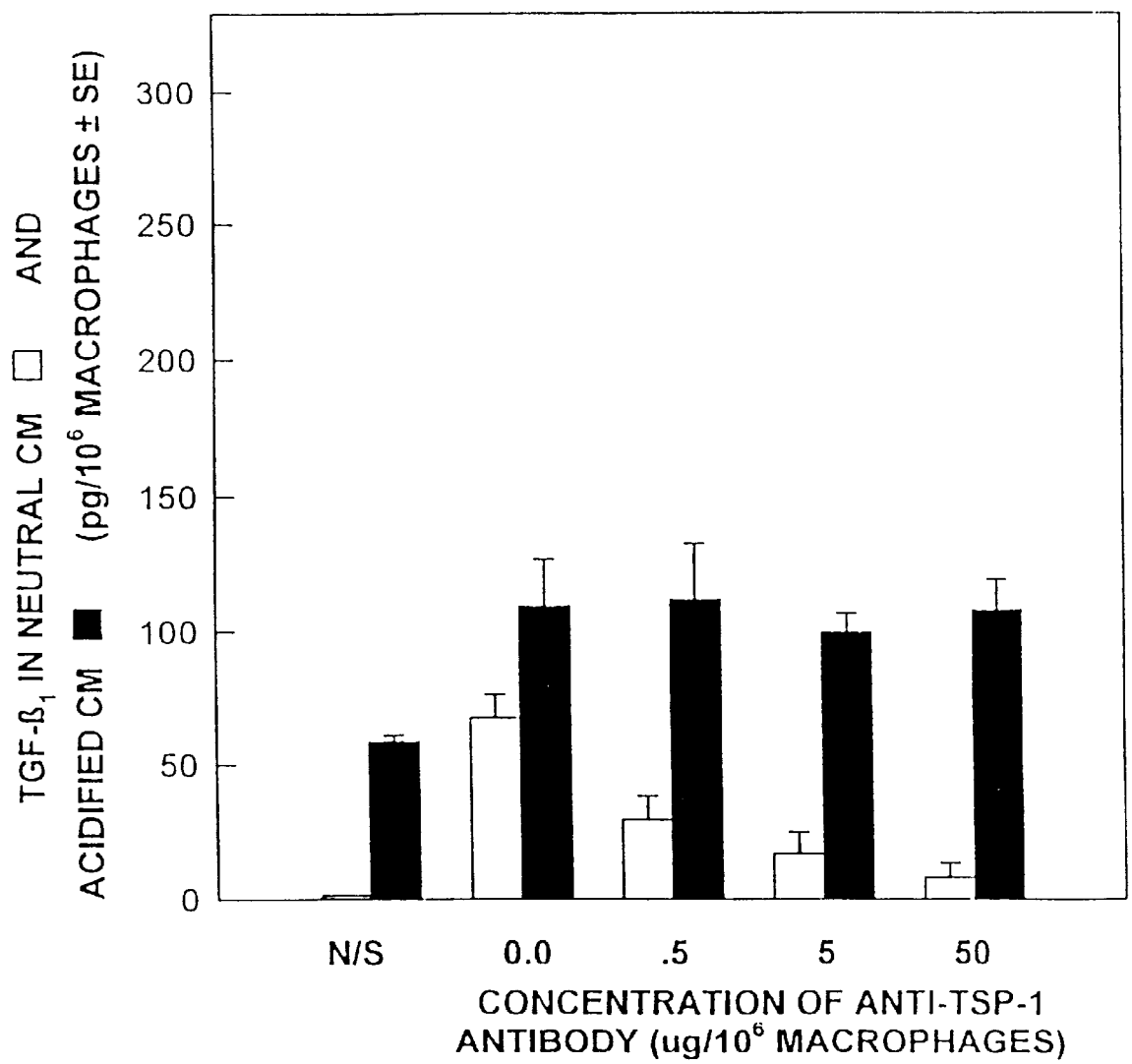

To determine if the presence of TSP-1 in the conditioned medium was important to the activation of L-TGF-$\beta_1$, the alveolar macophages were cultured in the absence and presence of anti-TSP-1 antibody. When present, anti-TSP-1 inhibited the activation of L-TGF-$\beta_1$ but had no effect on the secretion of the latent form of TGF-$\beta_1$ (FIG. 3). The presence of anti-TSP-1 antibody had no effect on the quantity of plasmin generated by the alveolar macrophages, suggesting that in the absence of TSP-1, plasmin alone cannot activate L-TGF-$\beta_1$ and therefore both plasmin and TSP-1 are required to be present to activate L-TGF-$\beta_1$.

Figure 4A:
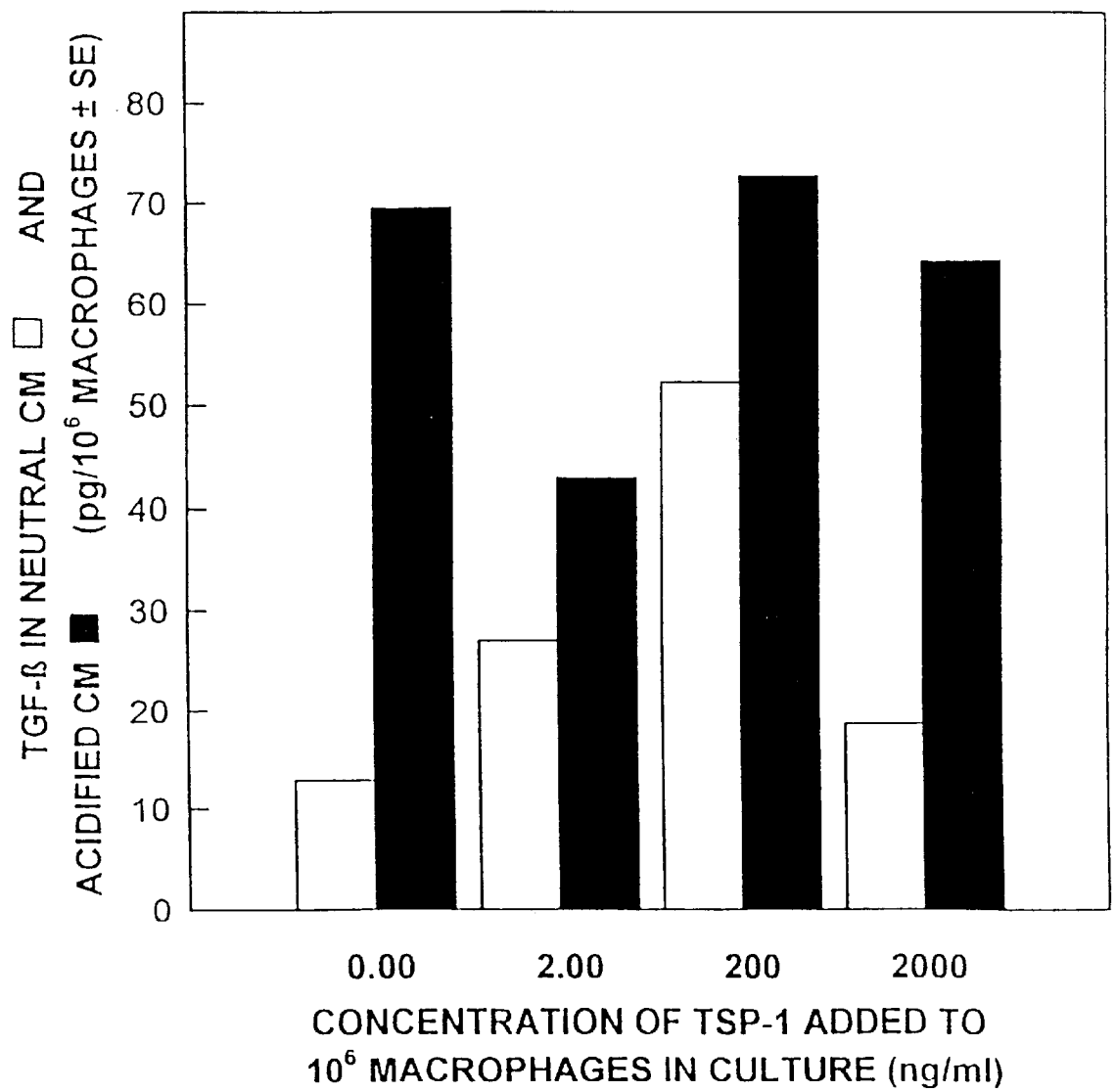
Figure 4B:
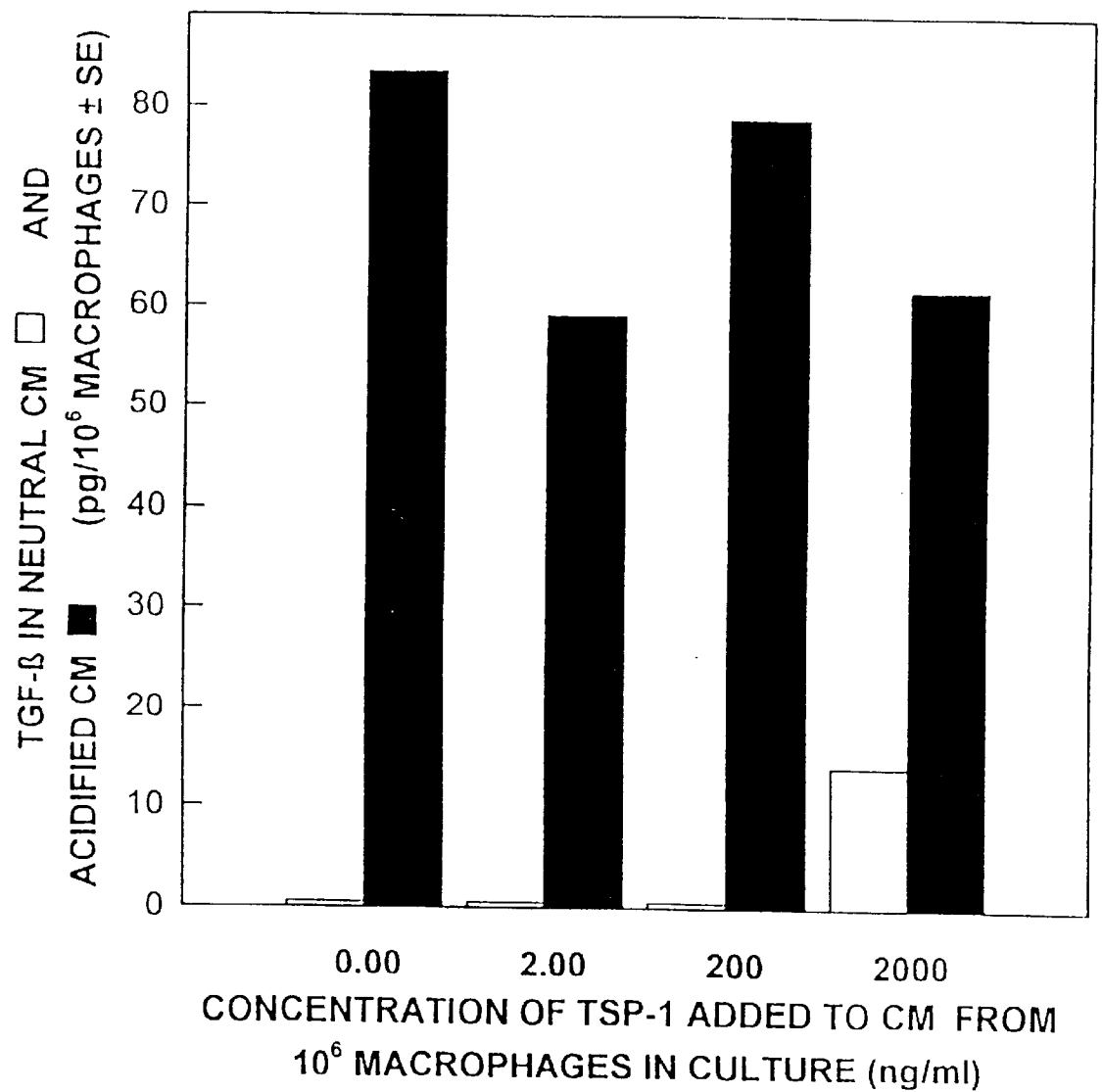

Since TSP-1 has been reported to activate L-TGF-$\beta_1$ in solution, it was next determined if alveolar macrophage derived L-TGF-$\beta_1$ could be activated in the presence of purified TSP-1. It had been previously demonstrated that after 12 hours in culture, alveolar macrophages activated by bleomycin injury secreted large quantities of L-TGF-$\beta_1$ into the conditioned media (CM). The addition of TSP-1 to cell free CM resulted in activation of the accumulated L-TGF-$\beta_1$ only at a very high dose of TSP-1 (FIG. 4A,B). However, all quantities of TSP-1 added to the CM overlying the alveolar macrophages was effective in activation of L-TGF-$\beta_1$ (FIG. 4A,B). These findings suggested that TSP-1 was only effective on alveolar macrophage derived L-TGF-$\beta_1$ in solution in very high doses. However all concentrations of TSP-1 were very effective in the presence of intact macrophages. Although the presence of both TSP-1 and plasmin is required for the activation of alveolar macrophage derived L-TGF-$\beta_1$, the results were in agreement with previous reports that cell surface localization was necessary for effective activation of L-TGF-$\beta_1$.

Figure 5:
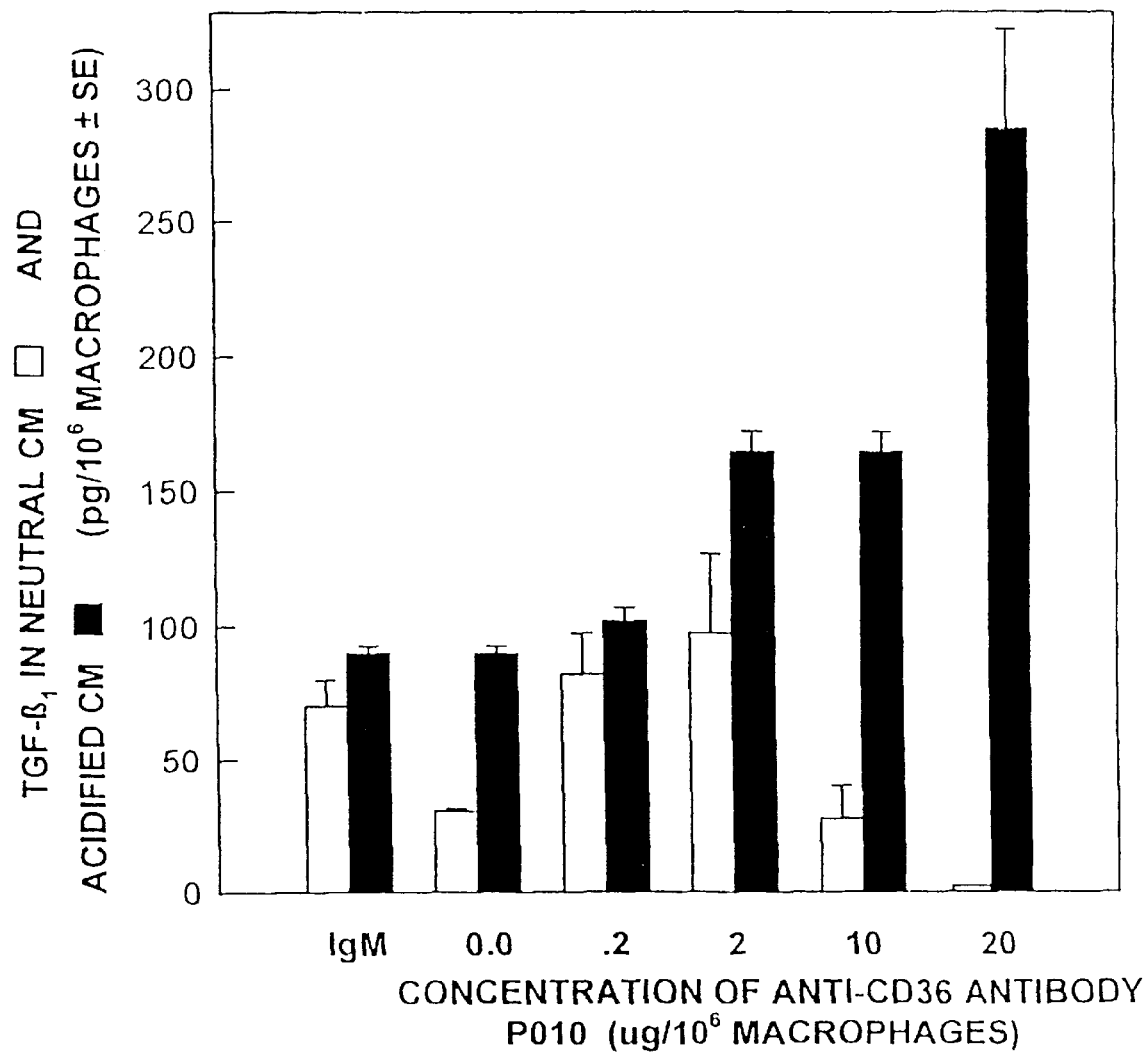
Figure 6B:
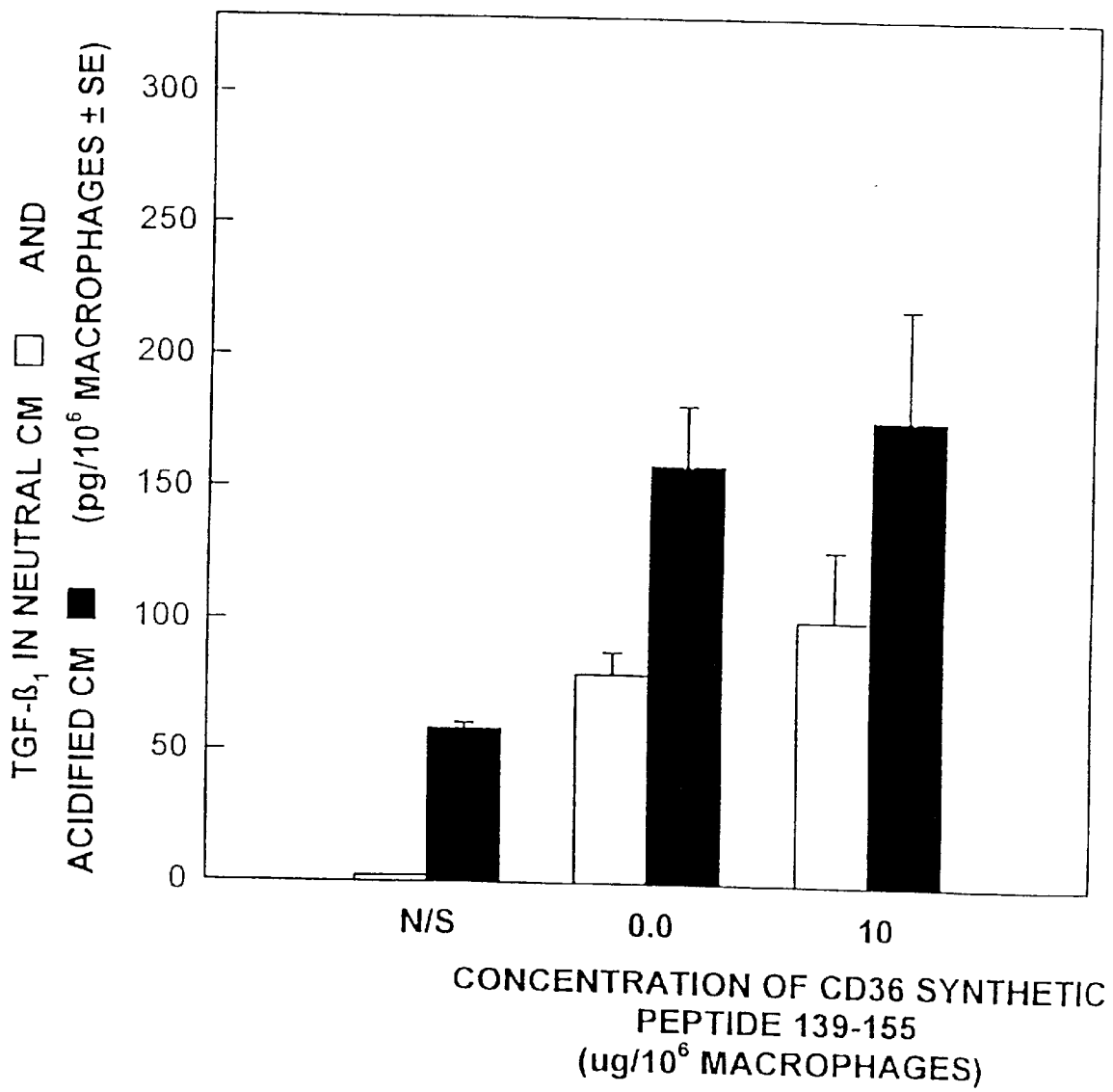
Figure 6C:
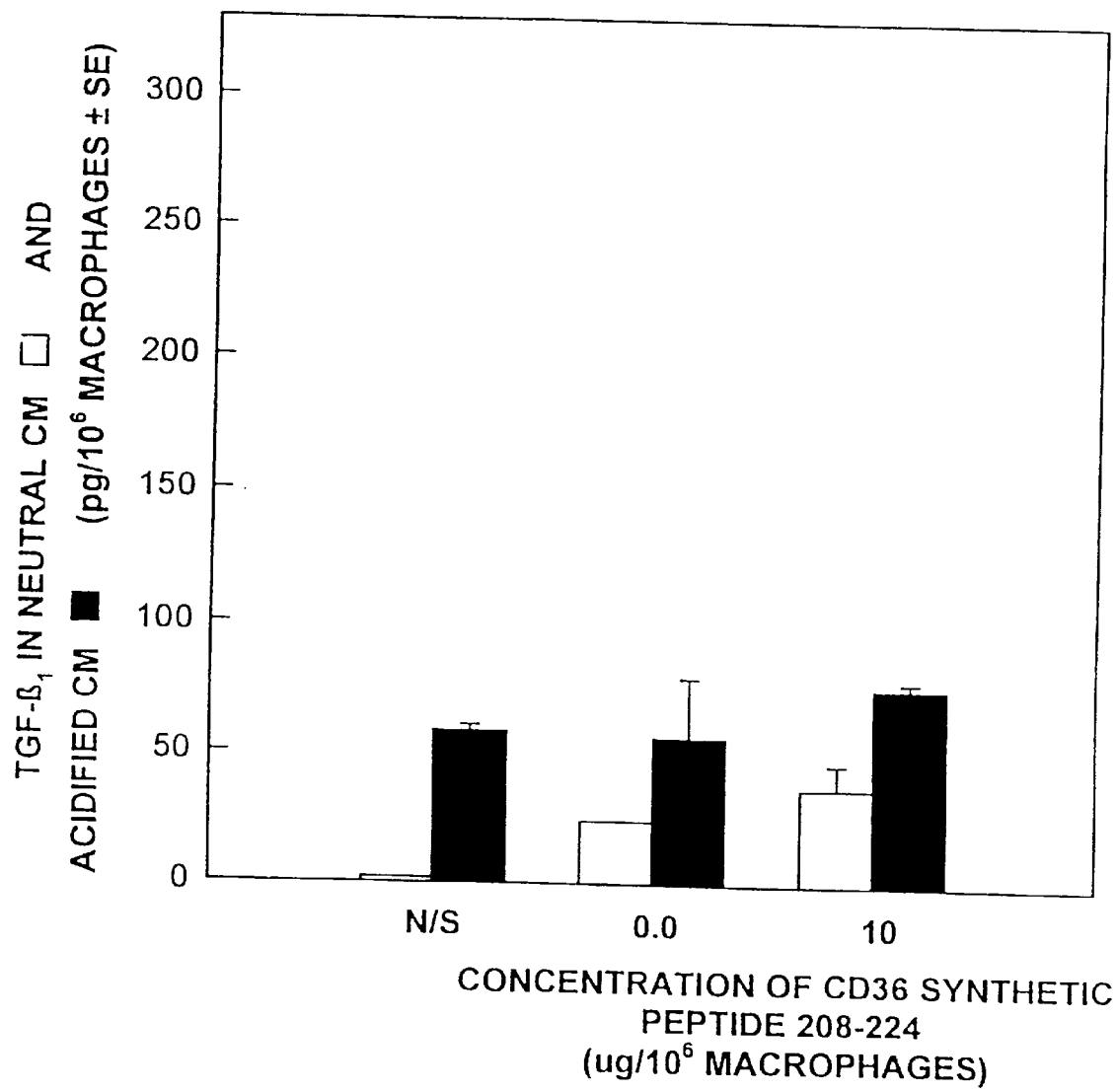
Figure 7A:
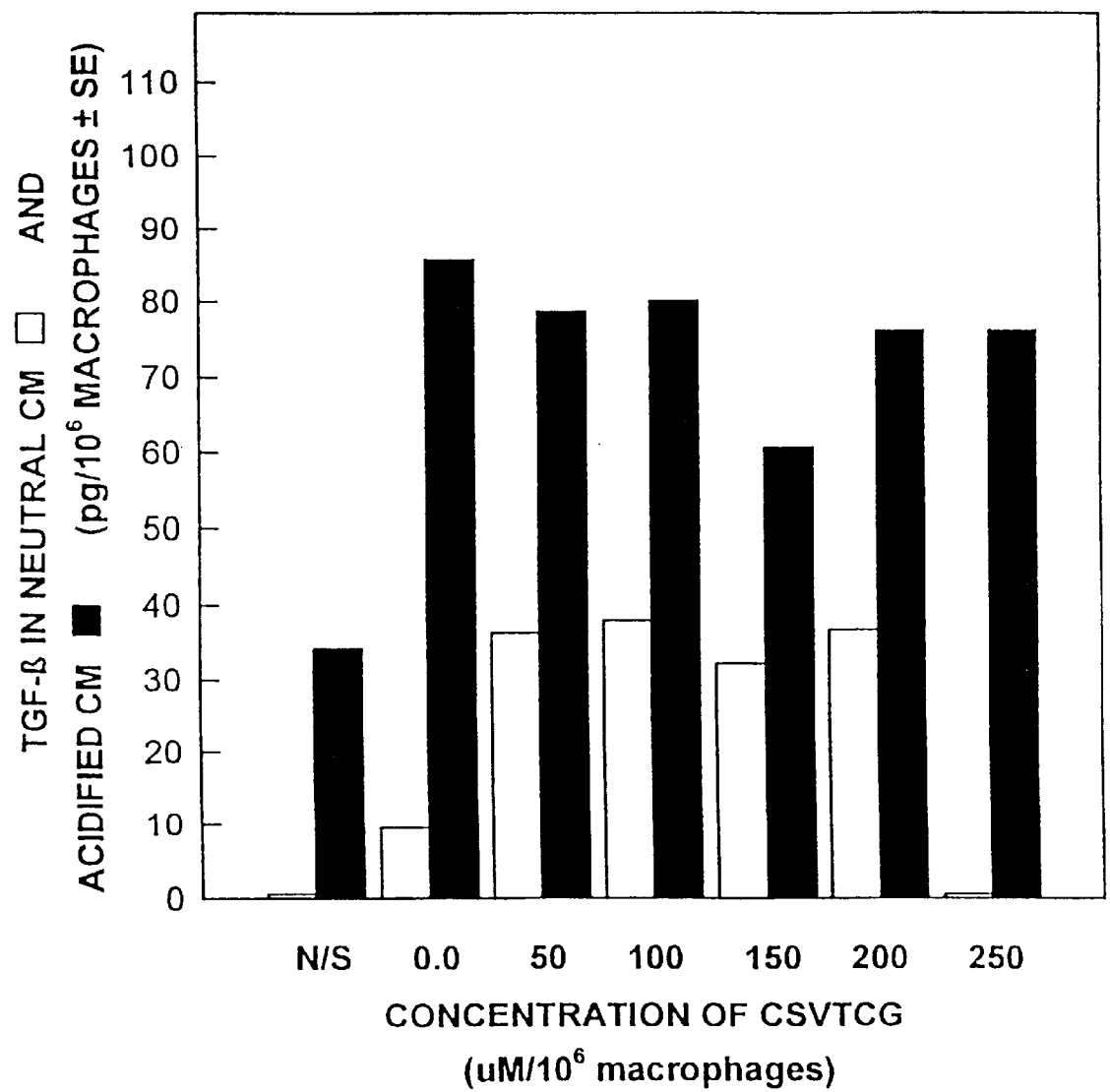
Figure 7B:
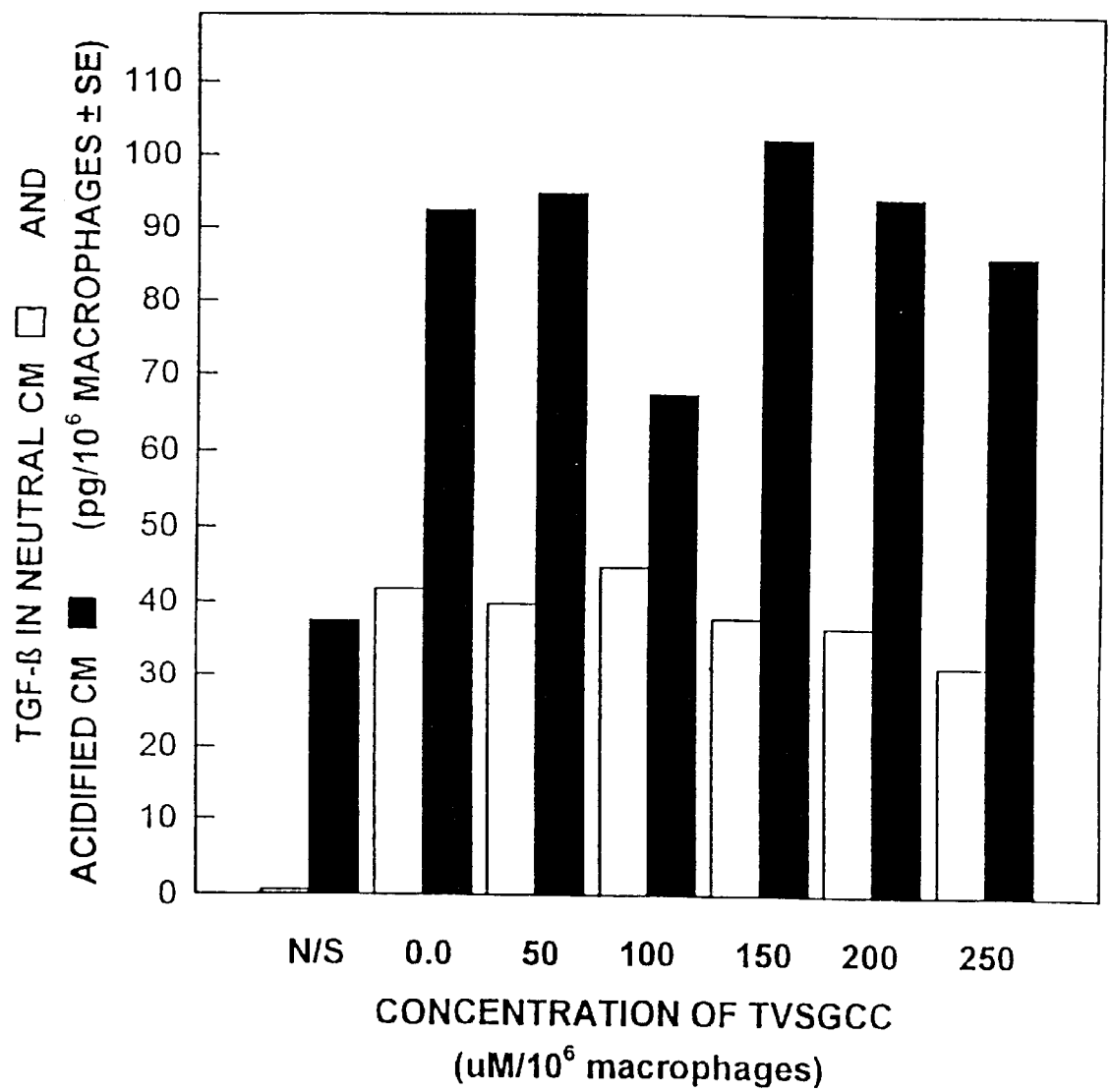

TSP-1 not only complexes with L-TGF-$\beta_1$, but can also bind to cell surface receptors such as CD36, which is prominently expressed on macrophages. It was next determined if the CD36 receptor was important in binding TSP-1 as part of the post-translational process of activation of L-TGF-$_1$. Antibodies specific to CD36 totally abrogated the activation of L-TGF-$\beta_1$ even though there was induction of secretion of total TGF-$\beta_1$ (FIG. 5). CD36 binding with TSP occurs at very specific sites on the extracellular domain of the CD36 molecule demarcated by amino acids 93–110. Binding of TSP-1 at this site stabilizes the interaction, while TSP-1 binding to CD36 at amino acids in the region demarcated by 139–155 enhances binding at the 93–110 region. However the amino acid sequences in CD36 from 204 to 248 have no effect on the binding of TSP to CD36. Synthetic peptides of the CD36 region 93–110 can prevent TSP binding to the CD36 receptor. When activated alveolar macrophages where incubated with the synthetic peptide mimicking the amino acids between 93–110 there was abrogation of activation of L-TGF-$\beta_1$ while the synthetic peptides mimicking the CD36 regions 139–155 and 204–288 had no effect on the activation of L-TGF-$\beta_1$ (FIG. 6A,B,C). The binding of TSP-1 to the receptor CD36 is through the six amino acid motif, CSVTCG on the TSP molecule. The presence of CSVTCG synthetic peptide prevents binding of TSP-1 to CD36. When activated alveolar macrophages were cultured in the presence of a high dose of the CSVTCG synthetic peptide there was no active TGF-$\beta_1$ present, while the quantity of L-TGF-$\beta_1$ was unchanged. When a scrambled peptide containing the same amino acids but in a different sequence (SVTGCC) was used as a control, there was no effect on the activation of L-TGF-$\beta_1$ (FIG. 7A,B).

Figure 9:
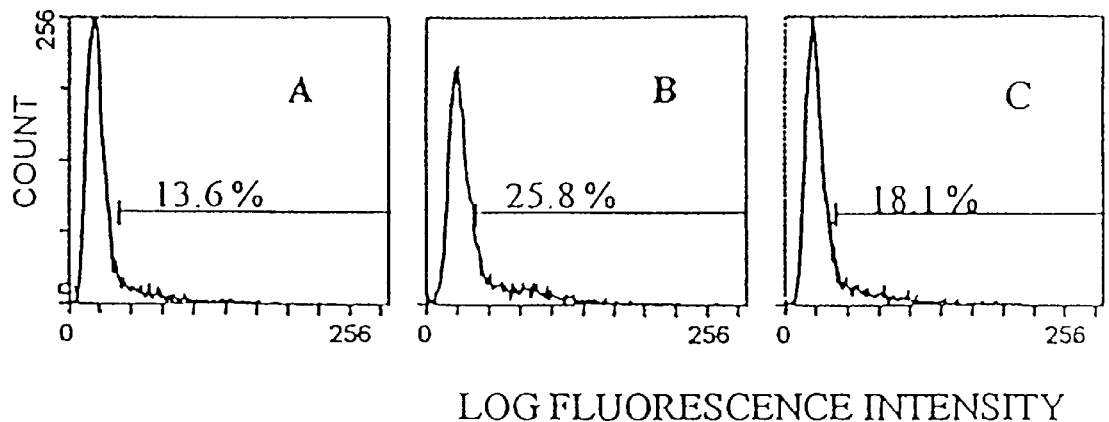
Figure 8:
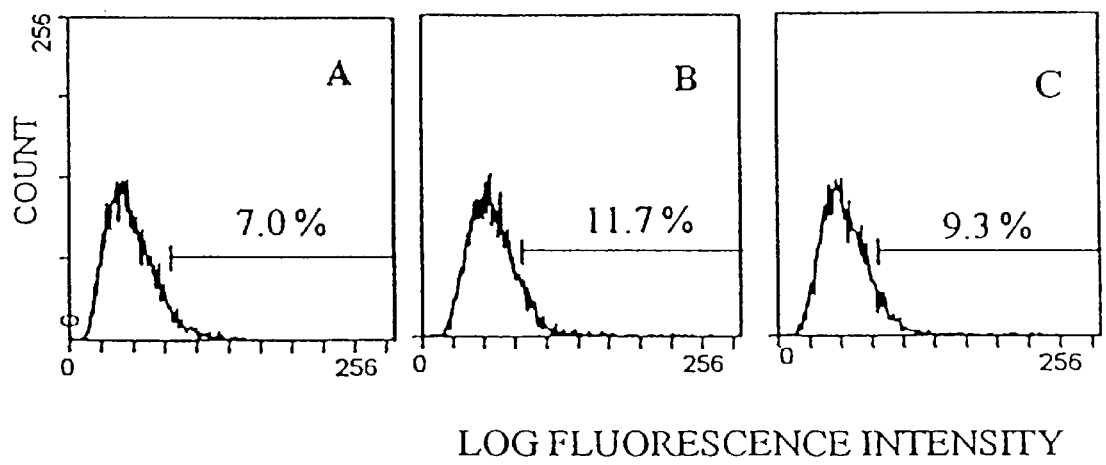

These observations suggest that association of L-TGF-$\beta_1$ to the alveolar surface by a CD36 receptor was necessary for adequate activation mediated by TSP-1 and plasmin to occur. However, the CD36 receptor has not been reported to bind L-TGF-$\beta_1$, but it does bind TSP-1 which can complex with L-TGF-$\beta_1$. In addition, the presence of TSP-1 appears to be necessary for activation of alveolar macrophages derived L-TGF-$\beta_1$. The most likely explanation of these findings is that L-TGF-$\beta_1$ complexes with TSP-1 prior to its association with the macrophages. The cell surface localization of L-TGF-$\beta_1$ then must occur by its association with TSP-1. This then suggests that TSP-1 must bind to the cell surface of the macrophage during the process of activation of L-TGF-$\beta_1$. To demonstrate that after bleomycin induced injury, alveolar macrophages have surface associated TSP-1, FACS analysis and anti-TSP-1 antibodies in the absence or presence of a 93–110 CD36 synthetic peptide which had been previously demonstrated to interfere with TSP-1 binding to CD36 were used. It was demonstrated that small quantities of TSP-1 were present on the cell surface of alveolar macrophages after normal saline treatment and the presence of CD36 synthetic peptide, 93–110, decreased the TSP-1 on the cell surface by a minimal amount (FIG. 8A–C). However, alveolar macrophages obtained after bleomycin administration had almost a 2 fold increase in TSP-1 cell surface association (FIG. 9A–C) while the presence of the CD36 synthetic peptide 93–110, a condition that abrogates the association of the TSP-1 molecule with the cell surface CD36 receptor, diminished the TSP-1 on the cell surface by 50%.

Taken together, the findings suggest that TSP-1 in the conditioned media associates with alveolar macrophages L-TGF-$\beta_1$ which then complexes with the TSP-1 cell surface receptor, CD36. This complex is then acted upon by plasmin which is generated by the cells themselves. Subsequently the mature TGF-$\beta_1$ is released into the CM (FIG. 10A,B) in the experimental situation, but would be released into its microenvironment in the in vivo setting.

EXAMPLE 2

Five patients with clinical criteria of idiopathic pulmonary fibrosis and 2 patients with no evidence of pulmonary inflammation or fibrosis were used in this preliminary study. High resolution computed axial tomography (HRCT) was performed on all IPF patients to determine the location of early and advanced changes. Bronchoalveolar lavage (BAL) was performed on the upper and lower lobes in patients with IPF. BAL of only the lower lobes was done on the control patients. The presence of TGF-$\beta$ isoforms in the cell free BAL fluid was determined using CCL-64 bioassay. Alveolar macrophages obtained from the BAL were cultured overnight and the conditioned media was collected for TGF-$\beta$ quantitation and isoform characterization.

The results of the human study are summarized in Tables 1 through 5.

TABLE 1

Transforming growth factor-beta (TGF-$\beta$) secreted by Alveolar Macrophages (AM).

| Diagnosis | Source of AM | TGF-$\beta$ secreted in the active form (fmoles ± SE/$10^6$ AM) | TGF-$\beta$ secreted in active and latent form (fmoles ± SE/$10^6$ AM) | % Active TGF-$\beta$ secreted by AM ± SE |
|---|---|---|---|---|
| IPF | Upper lobes | 2.55 ± 0.49 | 2.68 ± 0.50 | 96.6 ± 1.52 |
| IPF | Lower lobes | 2.64 ± 1.28 | 3.88 ± 1.28 | 73.3 ± 0.91 |
| Control | Lower lobes | 0.0 | 0.74 ± 0.23 | 0 |

TABLE 2

Isoforms of TGF-$\beta$ secreted by Alveolar Macrophages

| Diagnosis | Source of AM | TGF-$\beta_1$ % of total | TGF-$\beta_2$ % of total | TGF-$\beta_3$ % of total |
|---|---|---|---|---|
| IPF | Upper lobes | not yet done | | |
| IPF | Lower lobe | 72 | 0 | 11.9 |
| Control | Lower lobe | 15 | 29.5 | 55.5 |

TABLE 3

Inhibition of the secretion of active TGF-β secreted by AM from 2 patients with IPF

| Inhibitor Used | % of inhibition ± SE of active-TGF-β compared to condition when no inhibitor was present |
|---|---|
| Anti-thrombospondin-1 (α-TSP-1) | 71 |
| Alpha$_2$-antiplasmin (α$_2$-AP) | 89.5 ± 7.4 |
| Anti-CD36 antibody (α-CD36) | 93.5 ± 5.3 |
| CD36 synthetic peptide (amino acids 93–110) | 76.5 ± 16.6 |

α-TSP-1 and α$_2$-AP are commercially available from Sigma. Anti-CD36 antibody is commercially available from a number of sources. CD36 synthetic peptides were made by us at the Manitoba Institute of Cell Biology.

TABLE 4

Transforming growth factor-beta (TGF-β) present in the bronchoalveolar lavage fluid (BALF).

| Diagnosis | Source of BALF | TGF-β in the active form (fmole ± SE/ml) | TGF-β in the active and latent form (fmole ± SE/ml) | % active TGF-β present |
|---|---|---|---|---|
| IPF | Upper lobes | 1.05 ± 0.15 | 4.83 ± .58 | 30.4 ± 4.10 |
| IPF | Lower lobes | 2.1 ± 0.38 | 4.690 ± 0.62 | 56.0 ± 6.81 |
| Control | Lower lobes | 0.0 | 2.08 ± 0.33 | 0.0 |

TABLE 5

Isoforms of TGF-β in the BALF

| Diagnosis | Source of BALF | TGF-β$_1$ | TGF-β$_2$ | TGF-β$_3$ |
|---|---|---|---|---|
| IPF | Upper lobes | 100% | 0 | 0 |
| IPF | Lower lobes | 69% | 19% | 12% |
| Control | Lower lobes | 100% | 0 | 0 |

Alveolar macrophages from normal human patients secrete no active TGF-β and only secrete small quantities of latent TGF-β. However, alveolar macrophages from patients with IPF secrete not only increased amounts of TGF-β, but up to 96.6% of the TGF-β is in its active form. The secretion of this active TGF-β by human alveolar macrophages can be inhibited by the presence of applicants' synthetic CD36 peptide. Furthermore, the cell free fluid derived from the lower lobes of patients with IPF contains a lot of active TGF-β that could be from the epithelial cells and alveolar macrophages. For this reason, it is necessary to inhibit the secretion of TGF-β by alveolar macrophages and alveolar epithelial cells.

Based on human and animal studies, applicants have demonstrated that TGF-β$_2$ and TGF-β$_3$ are ubiquitously expressed in all lung cells while TGF-β$_1$ expression in epithelial cells occurs only in those situations where there is recurrent or chronic injury and repair. Applicants findings suggest that the increased expression of TGF-β$_1$ in epithelial cells in fibrotic lung diseases is not disease-specific but occurs as a consequence of the chronicity of the injury.

Applicants' work demonstrates that alveolar macrophages and alveolar epithelial cells aberrantly produce TGF-β$_1$ in IPF and other progressive fibrotic diseases. Reduction in alveolar macrophage and epithelial cell secretion of active TGF-β$_1$ would result in: 1) decrease in inflammation, 2) decrease in subepithelial connective tissue synthesis and fibrosis, and 3) decrease in intraalveolar fibrosis. All three of these pathological processes are a hallmark of progressive pulmonary fibrosis. Based on applicants' animal studies, a CD36 peptide of the smallest size and/or the one least associated with side effects or complications will be delivered as an aerosol to the lungs, for example using a metered dose inhaler containing the CD36 peptide.

Other applications for aerosolized CD36 peptide include:

1) Progressive asthma is unresponsive to inhaled bronchodilators and corticosteroids as well as systemic corticosteroids. The airways of patients who have died of progressive asthma have an increase in connective tissue which is a mark of permanent change. This connective tissue could be synthesized due to active TGF-β$_1$ present in the airway macrophages or airway epithelial cells. An inhaled inhibitor of TGF-β$_1$ should inhibit or retard enhanced connective tissue synthesis and progression of this form of asthma.

2) Lung transplantation has improved the mortality rate from lethal lung diseases. However a common complication of lung transplantation is bronchiolitis obliterans that is progressive and lethal once it occurs. The lesion is characterized by inflammation and connective tissue synthesis in small airways. Based on applicants' findings of epithelial cells being a potent source of active TGF-β$_1$ and TGF-β$_3$, an increased production and secretion of active TGF-β is expected in transplanted lungs. Aerosolized CD36 peptide as an inhibitor of TGF-activation would then be expected to reduce or ameliorate the endobronchial inflammation and fibrosis seen in this setting.

There are a number of disorders that are characterized by increased inflammation and relentless fibrosis. In most of these disorders the presence of active TGF-β may be important in the pathogenesis.

Some examples follow:

TABLE 6

| DISEASE | FORM OF DELIVERY OF CD36 PEPTIDE |
|---|---|
| 1. Chrons disease | Enema |
| 2. Rheumatoid arthritis | Parenteral intraarticular injection |
| 3. Keloids and post-burn hypertrophic scarring | Emolient skin cream |
| 4. Post abdominal surgery adhesions | Peritoneal lavage with aqueous suspension |

What is claimed is:

1. A method of inhibiting the activation of latent-transforming growth factor-beta 1 in a mammal, which activation is associated with an inflammatory or fibrotic disease, comprising administering to a mammal a synthetic or natural CD36 peptide.

2. The method according to claim 1, wherein the disease is selected from idiopathic pulmonary fibrosis, scleroderma, systemic lupus erythematosis, sarcoidosis, silicosis, asbestosis, hypersensitivity pneumonitis, tuberculosis, keloids, burn induced hypertrophic scarring, cirrhosis of the liver, hypertrophic retinopathy, hypertrophic vetrinopathy, rheumatoid arthritis, Chron's disease, and restenosis of vessels after angioplasty, vascular surgery, or vascular injury.

3. The method according to claim 1, wherein the disease is idiophathic pulmonary fibrosis.

4. The method according to claim 1, wherein said mammal is human.

5. The method according to claim 1, wherein the peptide corresponds substantially to the CD36 93–110 region.

6. The method according to claim 5, wherein the disease is selected from idiopathic pulmonary fibrosis, scleroderma, systemic lupus erythematosis, sarcoidosis, silicosis, asbestosis, hypersensitivity pneumonitis, tuberculosis, keloids, burn induced hypertrophic scarring, cirrhosis of the liver, hypertrophic retinopathy, hypertrophic vetrinopathy, rheumatoid arthritis, Chron's disease, and restenosis of vessels after angioplasty, vascular surgery, or vascular injury.

7. A method of inhibiting the activation of latent-transforming growth factor-beta 1 in a mammal, which activation is associated with an inflammatory or fibrotic disease, comprising administering to a mammal a monoclonal antibody selected from antibodies to CD36 and antibodies to thrombospondin-1.

8. A method of inhibiting the activation of latent-transforming growth factor beta 1 in a mammal, which activation is associated with an inflammatory or fibrotic disease, comprising administering to a mammal a peptidesequence defined by SEQ ID NO:1.

9. A method of inhibiting the activation of latent-transforming growth factor-beta 1 in a mammal, which activation is associated with metastatic breast cancer, comprising administering to a mammal a synthetic or natural CD36 peptide or fragment thereof.

* * * * *

UNITED STATES PATENT AND TRADEMARK OFFICE
CERTIFICATE OF CORRECTION

PATENT NO.     : 6,090,367
DATED          : July 18, 2000
INVENTOR(S)    : Nasreen Khalil It is certified that error appears in the above-identified patent and that said Letters Patent is hereby corrected as shown below:

Title page,
Item [60], in the Related U.S. Application Data section, please insert:
-- Continuation of international application no. PCT/CA96/00311 filed May 17, 1996. --; and
Item [30], in Foreign Application Priority Data section, delete
"May 17, 1996  [CA]  Canada ........................
PCT/CA96/00311"

Column 1,
Line 4, after the TITLE, but prior to the BACKGROUND OF THE INVENTION, please insert the following new paragraph:
-- This application is a continuation of international PCT application PCT/CA96/00311 filed on May 17, 1996. --

Column 16,
Lines 4-5, replace "peptidese-quence" with -- peptide sequence --.

Signed and Sealed this

Eighteenth Day of June, 2002

Attest:

JAMES E. ROGAN
Attesting Officer        Director of the United States Patent and Trademark Office

SEQUENCE LISTING

```
<160> NUMBER OF SEQ ID NOS: 1

<210> SEQ ID NO 1
<211> LENGTH: 6
<212> TYPE: PRT
<213> ORGANISM: Artificial Sequence
<220> FEATURE:
<223> OTHER INFORMATION: Description of Artificial Sequence:  epitope of
      thrombospondin-1

<400> SEQUENCE: 1

Cys Ser Val Thr Cys Gly
  1               5
```